(12) United States Patent
Kim et al.

(10) Patent No.: US 11,981,780 B2
(45) Date of Patent: May 14, 2024

(54) POLYMERIC GEL AND PREPARATION METHOD THEREFOR, AND ARTICLE COMPRISING SAME

(71) Applicants: INSTITUTE FOR BASIC SCIENCE, Daejeon (KR); POSTECH ACADEMY-INDUSTRY FOUNDATION, Gyeongsangbuk-do (KR)

(72) Inventors: Won Jong Kim, Gyeongsangbuk-do (KR); Junghong Park, Daegu (KR)

(73) Assignees: INSTITUTE FOR BASIC SCIENCE, Daejeon (KR); POSTECH ACADEMY-INDUSTRY FOUNDATION, Gyeongsangbuk-Do (KR)

(*) Notice: Subject to any disclaimer, the term of this patent is extended or adjusted under 35 U.S.C. 154(b) by 1245 days.

(21) Appl. No.: 16/606,143

(22) PCT Filed: Apr. 18, 2018

(86) PCT No.: PCT/KR2018/004496
§ 371 (c)(1),
(2) Date: Oct. 17, 2019

(87) PCT Pub. No.: WO2018/194369
PCT Pub. Date: Oct. 25, 2018

(65) Prior Publication Data
US 2020/0040145 A1    Feb. 6, 2020

(30) Foreign Application Priority Data
Apr. 18, 2017    (KR) .................. 10-2017-0049976

(51) Int. Cl.
*C08J 3/075*    (2006.01)
*C08J 3/24*    (2006.01)
(Continued)

(52) U.S. Cl.
CPC ............... *C08J 3/075* (2013.01); *C08J 3/24* (2013.01); *F01N 11/00* (2013.01);
(Continued)

(58) Field of Classification Search
CPC .......... C08J 3/075; C08J 3/24; C08J 2387/00; F01N 11/00; F01N 2570/12; G02C 7/04
See application file for complete search history.

(56) References Cited

U.S. PATENT DOCUMENTS

2019/0046463 A1*    2/2019    Choi .................... A61K 31/405

FOREIGN PATENT DOCUMENTS

EP    1531757 A2    5/2005
EP    1993447 A2    11/2008
(Continued)

OTHER PUBLICATIONS

Kim et al ("Therapeutic-Gas-Responsive Hydrogel", Advanced Materials vol. 29, Issue 44 Nov. 2017). (Year: 2017).*
(Continued)

*Primary Examiner* — Robert S Jones, Jr.
*Assistant Examiner* — Jiangtian Xu
(74) *Attorney, Agent, or Firm* — NIXON PEABODY LLP

(57) ABSTRACT

The present invention relates to a polymeric gel comprising crosslink points, which are dissociated in response to nitrogen monoxide, and to a method for preparing a hydrogel, the method comprising the steps of: a) polymerizing a mixture of monomers comprising a monofunctional hydrophilic monomer and a monomer comprising a plurality of functional groups comprising an o-phenylenediamine residue; and b) separating a hydrogel formed by the polymerization.

13 Claims, 7 Drawing Sheets

(51) Int. Cl.
*F01N 11/00* (2006.01)
*G02C 7/04* (2006.01)

(52) U.S. Cl.
CPC ....... *C08J 2387/00* (2013.01); *F01N 2570/12* (2013.01); *G02C 7/04* (2013.01)

(56) References Cited

FOREIGN PATENT DOCUMENTS

| EP | 2496550 A2 | 9/2012 |
|---|---|---|
| EP | 2498763 A1 | 9/2012 |
| JP | 2006506335 A | 2/2006 |
| JP | 2009529668 A | 8/2009 |
| JP | 2013510175 A | 3/2013 |
| KR | 20140114953 A | 9/2014 |
| KR | 20160103647 A | 9/2016 |
| KR | 20170007857 A | 1/2017 |

OTHER PUBLICATIONS

Supplementary European Search Report for Application No. 18 787 689.1 dated Dec. 10, 2020.
Mark J. S. Miller et al., "Nitric Oxide as a Mediator of Inflammation ?—You had better believe it", Mediators of Inflammation, vol. 4, 1995, Rapid Science Publisher, pp. 387-396.
Junhong Part et al., "Therapeutic-Gas-Responsive Hydrogel", Advanced Materials, 2017, pp. 1-8.
Ian Appleton et al., "Induction of Cyclo-Oxygenase and Nitric Oxide Sythase in Inflammation", Advances in Pharmacology, vol. 35, pp. 27-77.
International Search Report in English for PCT/KR2018/004496, dated Aug. 14, 2018, 4 pages.
KR Notice of Allowance for Application No. 10-2017-0049976, dated Dec. 27, 2021.
CN Office Action and Search Report for Application No. 201880025391.9, dated Nov. 23, 2021.
Fabregat Victor et al., "Nitric oxide sensitive fluorescent polymeric hydrogels showing negligible interference by dhydroascorbic acid", European Polymer Journal, 55 (2014), pp. 108-113, Elsevier.
Korean Office Action for Application No. 10-2017-0049976, dated Jun. 9, 2021.

* cited by examiner

[FIG. 1]
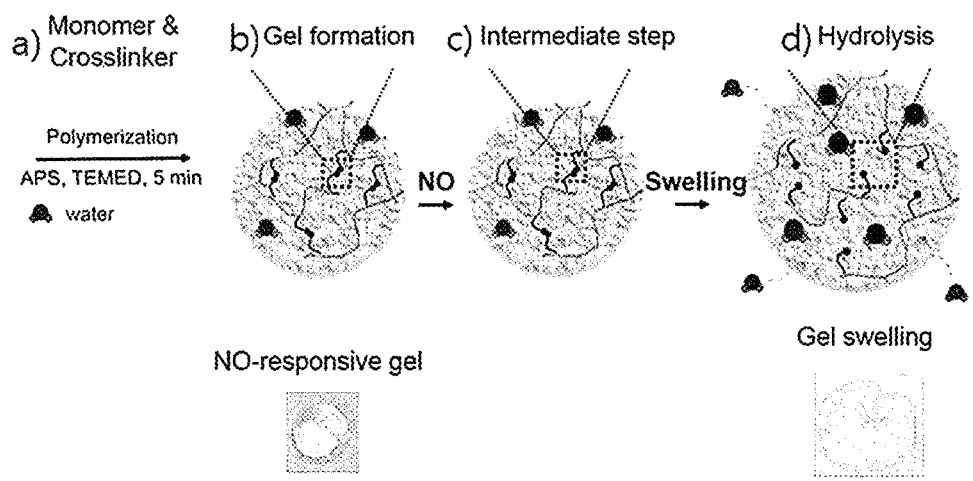
[FIG. 2]
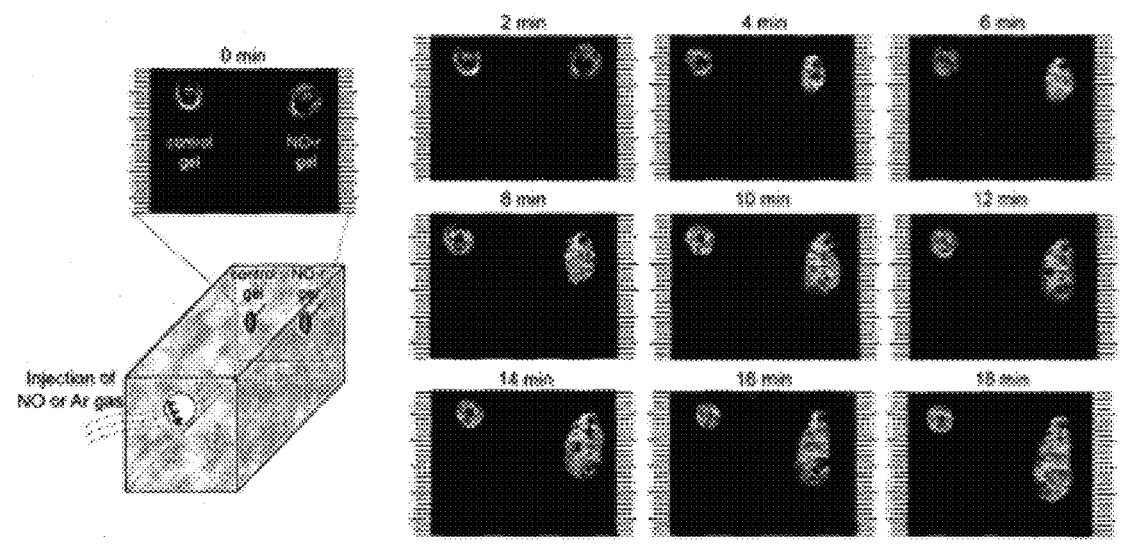

[FIG. 3]
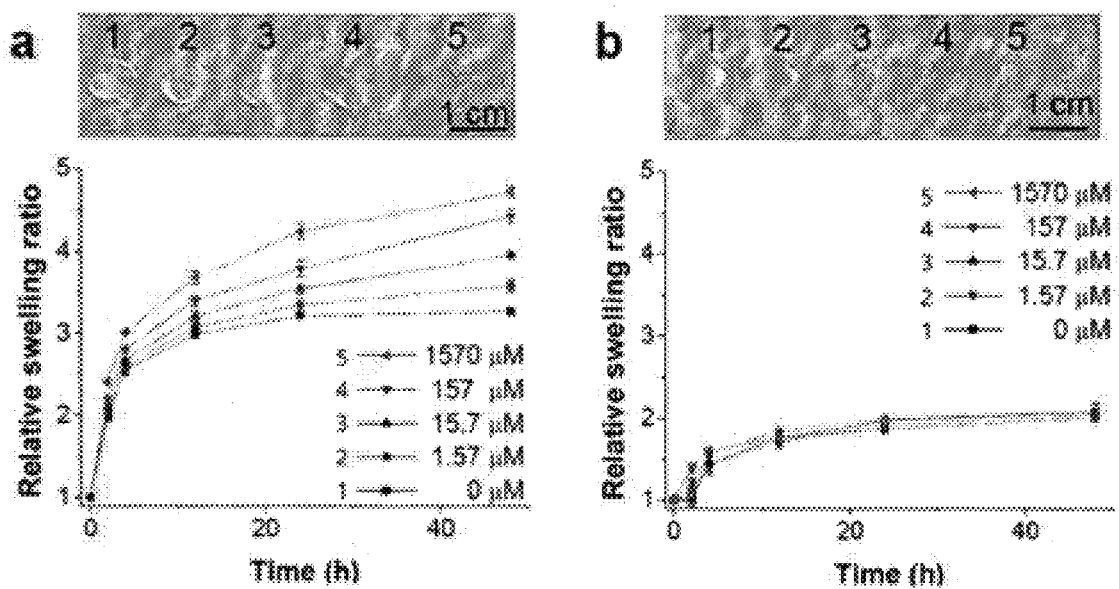
[FIG. 4]
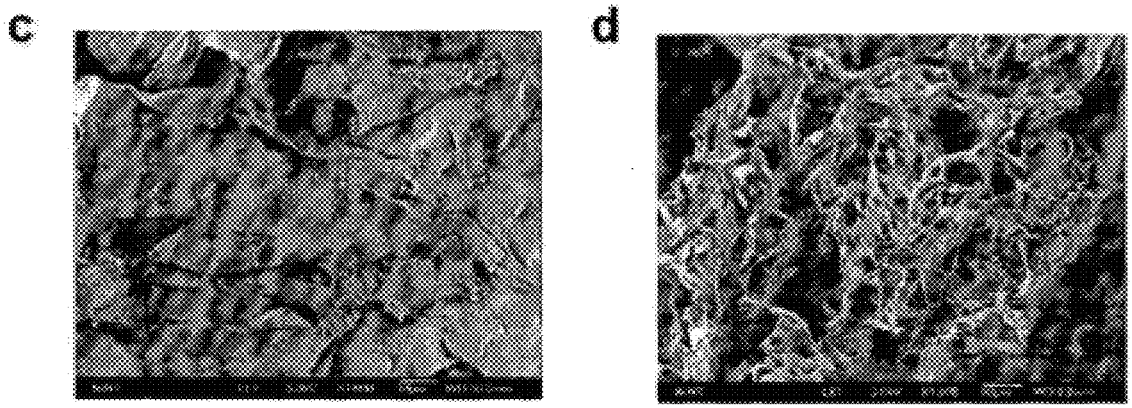

[FIG. 5]
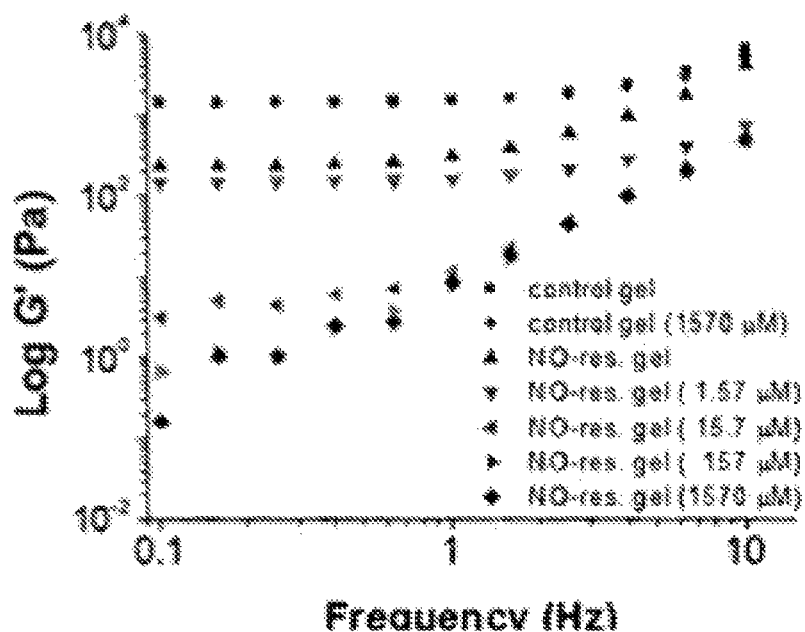
[FIG. 6]
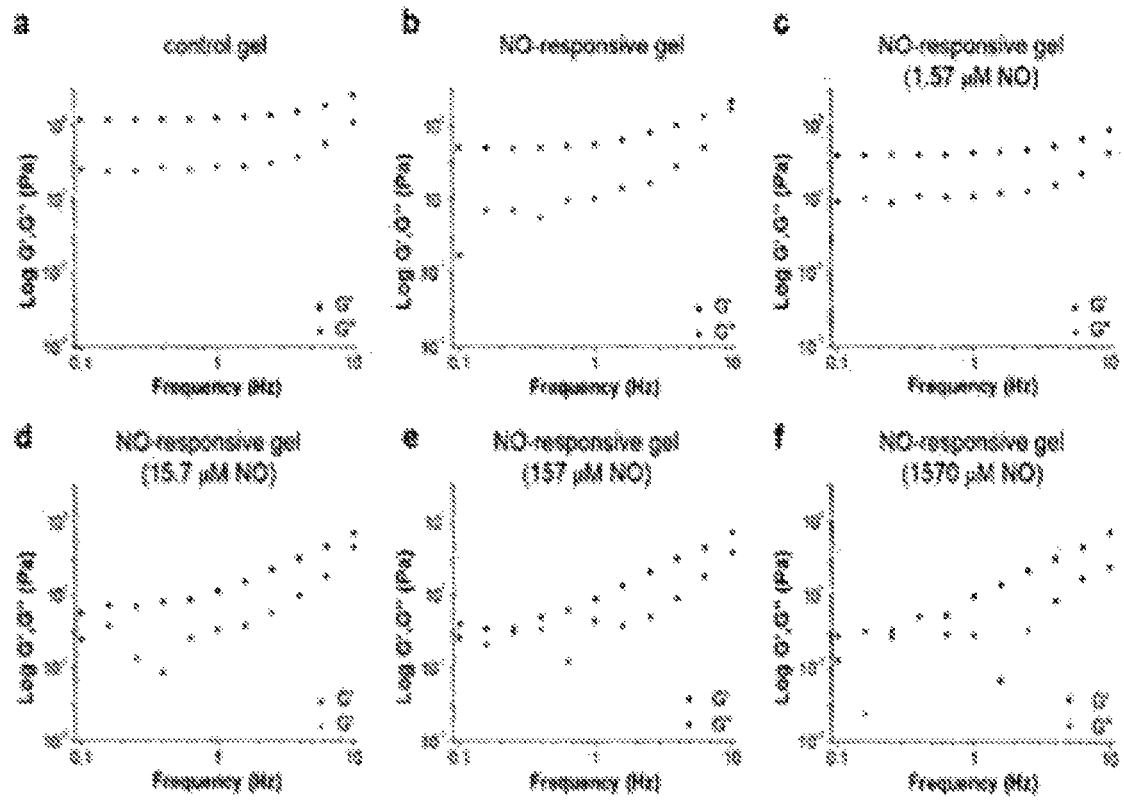

[FIG. 7]
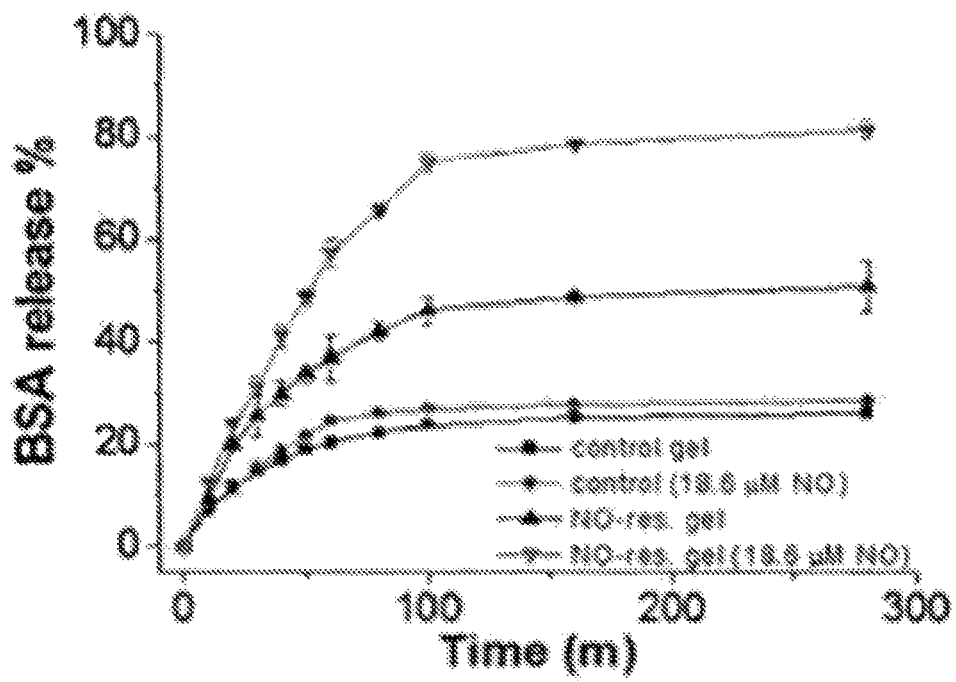

[FIG. 7]
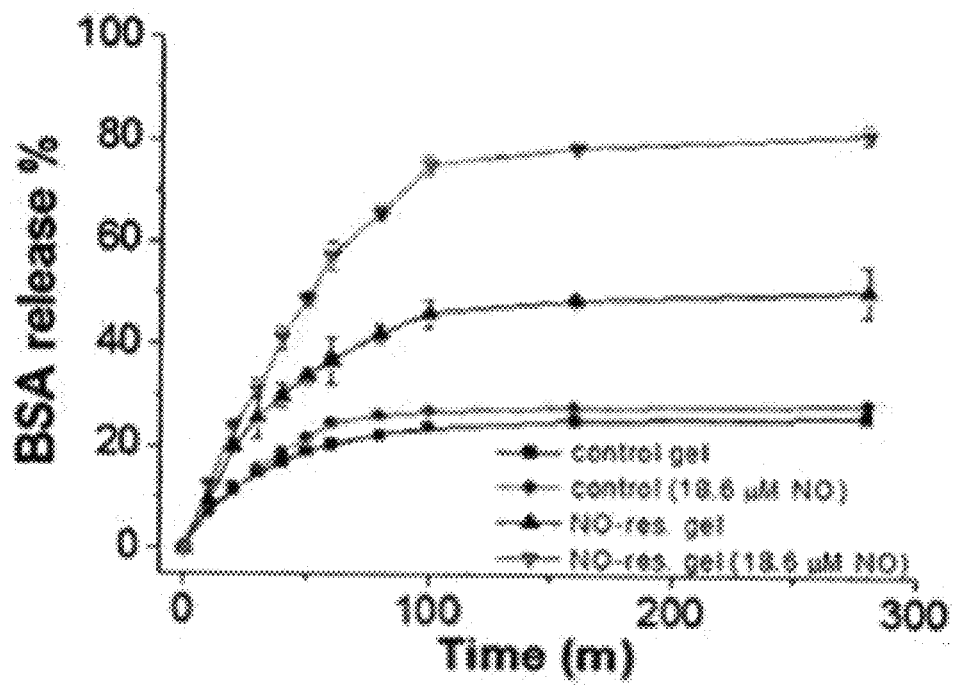

[FIG. 8]
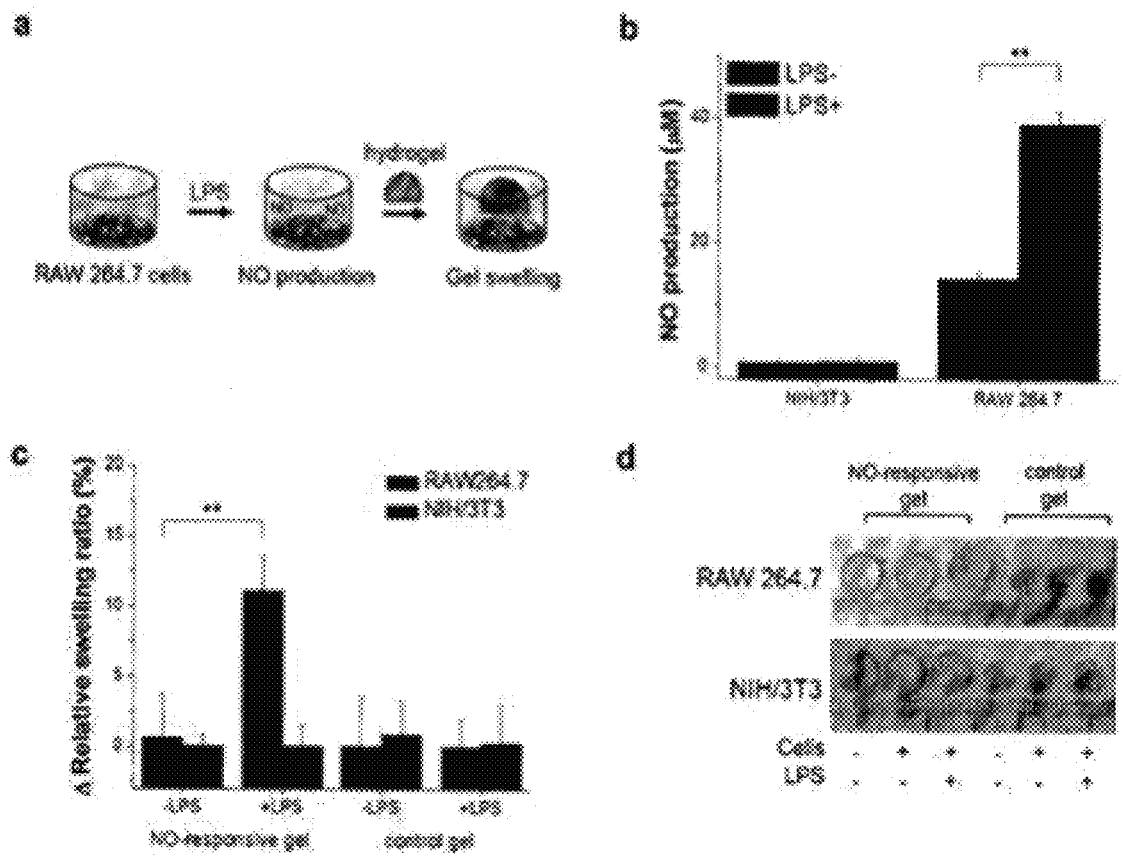
[FIG. 9]
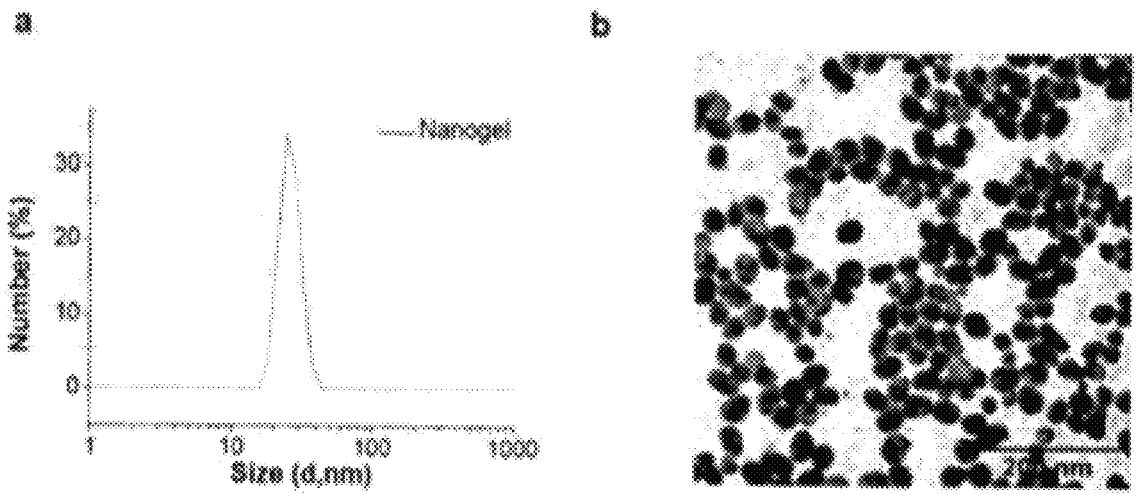

[FIG. 10]
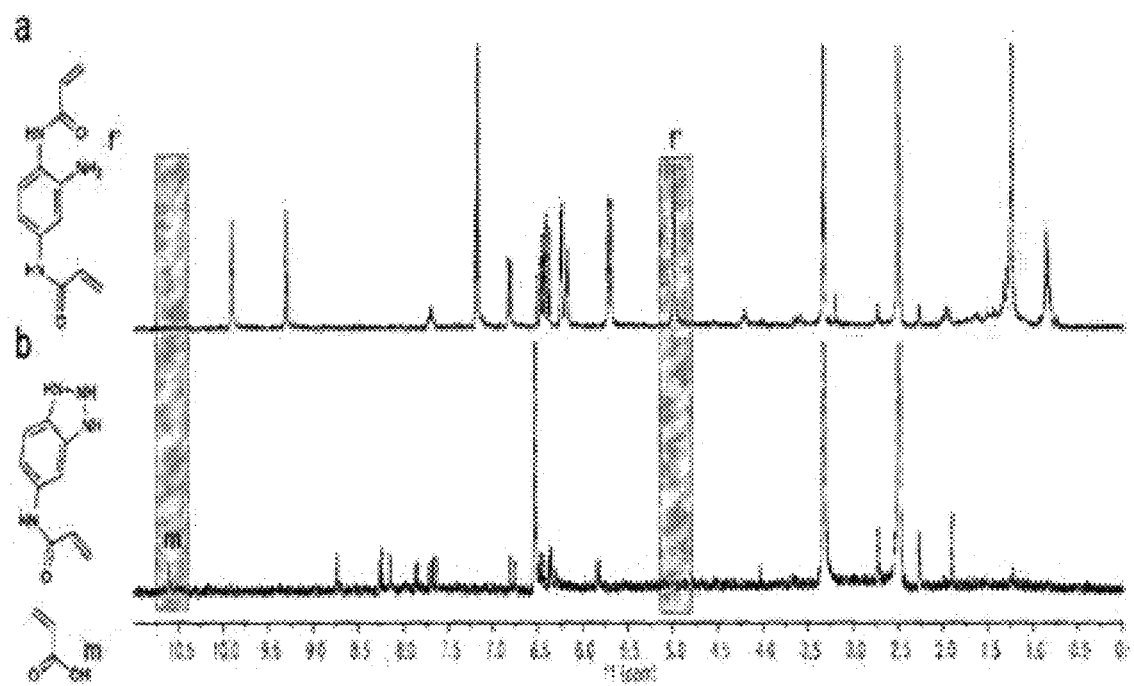

POLYMERIC GEL AND PREPARATION METHOD THEREFOR, AND ARTICLE COMPRISING SAME

This application is the United States National Phase filed under 35 U. S. C. § 365 of International Application filed under the Patent Cooperation Treaty ("PCT") serial number PCT/KR2018/004496, filed on Apr. 18, 2018, which in turn claims priority from KR application serial number 10-2017-0049976, filed Apr. 18, 2017, and the contents of which are herein incorporated by reference.

TECHNICAL FIELD

The present invention relates to a polymeric gel, a method of preparing the same, and an article including the same, and more particularly, to a polymeric gel which may react with nitrogen monoxide to remove nitrogen monoxide inside or outside a living body and may include a crosslinking point which is dissociated by response to nitrogen monoxide to effectively release a drug carried inside the polymeric gel, a method of preparing the same, and an article including the same.

BACKGROUND ART

Nitrogen monoxide (NO) is known as a signaling molecule which performs a key role in a cardiovascular system and is also known to perform various roles such as a neurotransmitter in a nervous system, a blood pressure regulator, and a blood flow regulator of various body organs.

According to recent research results, there are a few kinds of nitric oxide synthase (NOS) which is an enzyme producing nitrogen monoxide, and brain NOS (bNOS) existing in the brain, neuronal NOS (nNOS) existing in the nervous system, and endothelial NOS (eNOS) existing in the vascular system are always expressed at a certain level in the body, and nitrogen monoxide produced in a small amount by NOS plays an important role in maintaining homeostasis of the normal body, such as induction of neurotransmission or vasodilation.

However, nitrogen monoxide rapidly produced in a large amount by induced NOS (iNOS) derived by external stimulants or various cytokines is known to cause cytotoxicity or various inflammatory responses, and it has been studied that chronic inflammation is related to an increase of iNOS activity (Miller M. J. et al., Mediators of inflammation, 4, pp. 387-396, 1995; Appleton L. et al., Adv. Pharmacol., 35, pp. 27-28, 1996).

Accordingly, there is a need to develop a therapeutic agent which removes nitrogen monoxide and also releases a drug and the like carried inside in response to nitrogen monoxide, thereby being eventually used for therapeutic uses.

Also, nitrogen oxides (NOx) emitted in a large amount from automobile exhaust gas is mostly in the form of nitrogen monoxide, and development of a material which may effectively remove nitrogen monoxide is also currently needed.

DISCLOSURE

Technical Problem

An object of the present invention is to provide a polymeric gel having a crosslinked structure which may be effectively dissociated by a response to nitrogen monoxide, a method of preparing the same, and an article including the same.

Technical Solution

In one general aspect, a polymeric gel includes a crosslinking point which is dissociated in response to nitrogen monoxide.

In an exemplary embodiment, the crosslinking point may be derived from o-phenylenediamine, and specifically, the crosslinking point may satisfy the following Chemical Formula 1:

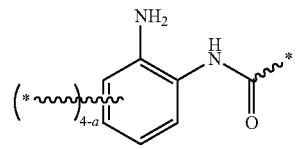

[Chemical Formula 1]

wherein * is a bonding site, and a is a real number of 0 to 3.

In an exemplary embodiment, the polymeric gel may be a hydrogel. Here, a polymer main chain of the hydrogel may be derived from a monofunctional hydrophilic monomer, and the hydrogel may be in the form of particles, a capsule, or a patch. In addition, the hydrogel may further include a second crosslinking point derived from a polyfunctional crosslinker containing two or more functional groups.

In another general aspect, a drug delivery system includes the polymeric gel.

In another general aspect, a method of preparing a hydrogel includes: a) polymerizing a mixture of a monofunctional hydrophilic monomer and a monomer containing a plurality of functional groups including an o-phenylenediamine residue; and b) separating the hydrogel formed by the polymerization, and the polymerization may be performed in a water phase.

In an exemplary embodiment, the monomer containing a plurality of functional groups including an o-phenylenediamine residue may satisfy the following Chemical Formula 2:

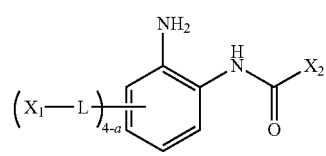

[Chemical Formula 2]

wherein L is —NHCO—, —RO—, —ORO—, or —RO(C=O)— in which R is a direct bond, a linear or branched alkylene group having 1 to 20 carbon atoms, an arylene group having 6 to 30 carbon atoms, a cycloalkylene group having 5 to 30 carbon atoms, an arylene group having 6 to 30 carbon atoms which is substituted with a linear or branched alkyl group having 1 to 20 carbon atoms, or a linear or branched alkylene group having 1 to 20 carbon atoms which is substituted with an aryl group having 6 to 30 carbon atoms, $X_1$ and $X_2$ are independently of each other —CH=$CH_2$ or —C($CH_3$)=$CH_2$, and a is a real number of 0 to 3.

In another exemplary embodiment, the monofunctional hydrophilic monomer and the monomer containing a plurality of functional groups including an o-phenylenediamine residue may be mixed at a molar ratio of 1000:0.289 to 2.89.

In another general aspect, a method of adjusting a mesh size of a reticular structure is performed by including an o-phenylenediamine residue as a crosslinking point of the reticular structure, and the mesh size may be selectively adjusted by nitrogen monoxide.

In another general aspect, a method of detecting nitrogen oxides in exhaust gas is performed by using the polymeric gel. Specifically, the nitrogen oxides may be nitrogen monoxide, and the polymeric gel may include 450 wt % or more of moisture based on a dried weight of the polymeric gel.

In still another general aspect, a contact lens includes the polymeric gel, and the contact lens may be for inhibiting angiogenesis.

Advantageous Effects

The polymeric gel according to the present invention includes a crosslinking point which is dissociated in response to nitrogen monoxide, and thus, it is possible for the polymeric gel to respond to nitrogen monoxide to remove unnecessary nitrogen monoxide inside and outside the body. Besides, a crosslinking point forming a crosslinked structure with a polymer chain of the polymeric gel is dissociated by response to nitrogen monoxide in an environment in which nitrogen monoxide is present, thereby releasing a drug carried inside the gel.

DESCRIPTION OF DRAWINGS

FIG. 1 schematically illustrates a method of preparing a polymeric gel according to an exemplary embodiment of the present invention and a process in which a crosslinking point of the polymeric gel is dissociated in response to nitrogen monoxide.

FIG. 2 is photographs in which gaseous nitrogen monoxide is reacted with a gel of Example 1 (NO-responsive gel) and a gel of Comparative Example 1 (control gel) and then the physical properties of the polymeric gel were evaluated.

FIG. 3 is a data showing a relative swelling ratio of each gel of Example 1(a) and Comparative Example 1(b) with concentrations of a nitrogen monoxide solution being varied.

FIG. 4 is scanning electron microscope (SEM) images before treatment (c) and after treatment (d) with a nitrogen monoxide solution, respectively.

FIG. 5 is a data showing log values of a modulus of elasticity (G') depending on concentration and frequency change of nitrogen monoxide solutions of Example 1 (NO-responsive gel) and Comparative Example 1 (control gel).

FIG. 6 is a data showing log values of a modulus of elasticity (G') and log values of a loss factor (G"), respectively, depending on concentration and frequency change of nitrogen monoxide solutions of Example 1 (NO-responsive gel) and Comparative Example 1 (control gel). A drawing in which the concentration of the nitrogen monoxide solution is not indicated means treatment only with water.

FIG. 7 is a data showing a degree of releasing BSA depending on treatment with water or a nitrogen monoxide solution over time, in a NO-responsive gel and a control gel.

In FIG. 8, a schematically illustrates a process in which RAW 264.7 cells are treated with LPS and reacted with the gel of Example 1, b is a data showing nitrogen monoxide production concentrations when untreated with LPS (LPS−) and when treated with LPS (LPS+), in each of RAW 264.7 cells and NIH/3T3 cells, c represents relative swelling ratios of gels when each gel of Example 1 (NO-responsive gel) and Comparative Example 1 (control gel) was incubated with each of LPS-untreated (−LPS) RAW 264.7 cells or NIH/3T3 cells and LPS-treated (+LPS) RAW 264.7 cells, and d is a real photograph of the gel after each gel of Example 1 (NO-responsive gel) and Comparative Example 1 (control gel) is incubated with each of LPS-treated or untreated RAW 264.7 cells or NIH/3T3 cells.

FIG. 9 is a size distribution and a scanning electron microscope (SEM) image of hydrogel nanoparticles prepared in a nano-size according to Example 2.

In FIG. 10, a is $^1$H NMR data of Compound 4, and b is $^1$H NMR data of Compound 4 which was dissociated in response to nitrogen monoxide.

BEST MODE

Hereinafter, referring to accompanying drawings, a polymeric gel, a method of preparing the same, and an article including the same, according to the present invention will be described in detail. The drawings to be provided below are provided by way of example so that the spirit of the present invention is able to be sufficiently transferred to those skilled in the art to which the present invention pertains. Therefore, the present invention is not limited to the drawings provided below but may be embodied in many different forms, and the drawings suggested below may be exaggerated in order to clear the spirit of the present invention. In addition, like reference numerals denote like elements throughout the specification.

Technical terms and scientific terms used herein have the general meaning understood by those skilled in the art to which the present invention pertains unless otherwise defined, and a description for the known function and configuration obscuring the gist of the present invention will be omitted in the following description and the accompanying drawings.

The present invention provides a polymeric gel having a crosslinked structure which may be effectively dissociated by response to nitrogen monoxide, a method of preparing the same, and an article including the same, and provides a polymeric gel which may react with nitrogen monoxide to remove nitrogen monoxide inside or outside a living body and may include a crosslinking point which is dissociated by response to nitrogen monoxide to effectively release a drug carried inside the polymeric gel, a method of preparing the same, and an article including the same.

Specifically, the polymeric gel according to an exemplary embodiment of the present invention may include a crosslinking point which is dissociated in response to nitrogen monoxide, as shown in FIG. 1. As such, the polymeric gel has advantages that the polymeric gel may respond to nitrogen monoxide to remove unnecessary nitrogen monoxide inside and outside the body, and also a crosslinking point forming a crosslinked structure with a polymer chain of the polymeric gel is dissociated by response to nitrogen monoxide in an environment in which nitrogen monoxide is present, thereby releasing a drug carried inside the polymeric gel.

More specifically, in an exemplary embodiment of the present invention, the crosslinking point is not particularly limited as long as it has a chemical structure which may be dissociated in response to nitrogen monoxide, and specifically for example, the crosslinking point is derived from o-phenylenediamine. The crosslinking point derived from o-phenylenediamine may form an amide-substituted benzotriazole intermediate residue by a reaction with nitrogen monoxide, as shown in FIG. 1, and this intermediate residue is hydrolyzed to be decomposed into a benzotriazole residue and a carboxylic acid residue, respectively.

In a specific exemplary embodiment, the crosslinking point may satisfy the following Chemical Formula 1:

[Chemical Formula 1]

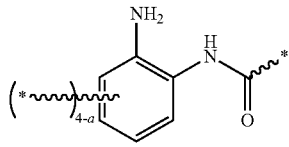

wherein * is a bonding site, and a is a real number of 0 to 3.

The polymeric gel includes the crosslinking point satisfying Chemical Formula 1, whereby the polymeric gel may effectively respond to nitrogen monoxide and the crosslinked structure may be easily dissociated after the response to nitrogen monoxide.

The crosslinking point may be formed from a monomer containing a plurality of functional groups including an o-phenylenediamine residue which is a crosslinker satisfying the following Chemical Formula 2:

[Chemical Formula 2]

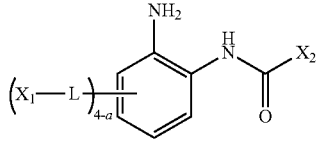

wherein L is —NHCO—, —RO—, —ORO—, or —RO(C=O)— in which R is a direct bond, a linear or branched alkylene group having 1 to 20 carbon atoms, an arylene group having 6 to 30 carbon atoms, a cycloalkylene group having 5 to 30 carbon atoms, an arylene group having 6 to 30 carbon atoms which is substituted with a linear or branched alkyl group having 1 to 20 carbon atoms, or a linear or branched alkylene group having 1 to 20 carbon atoms which is substituted with an aryl group having 6 to 30 carbon atoms, $X_1$ and $X_2$ are independently of each other —CH=$CH_2$ or —C($CH_3$)=$CH_2$, and a is a real number of 0 to 3.

More preferably, the monomer containing a plurality of functional groups including an o-phenylenediamine residue may satisfy the following Chemical Formula 3. By satisfying this, the crosslinker which may be dissociated by hydrolysis in response to nitrogen monoxide may be easily synthesized, and the polymeric gel may be easily prepared. In addition, selectivity and sensitivity to nitrogen monoxide may be excellent.

[Chemical Formula 3]

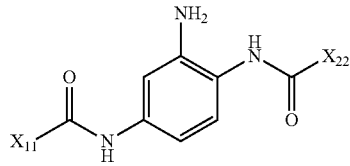

wherein $X_{11}$ and $X_{22}$ are independently of each other —CH=$CH_2$ or —C($CH_3$)=$CH_2$.

In a more specific exemplary embodiment, in a) of FIG. 1, the monomer and a crosslinker which are compounds represented by the following Chemical Formula 4 are included and polymerized, as shown in FIG. 1. Thus, in b) of FIG. 1, the polymeric gel including the crosslinking point derived from o-phenylene diamine and being represented by the following Chemical Formula 5 may be prepared.

[Chemical Formula 4]

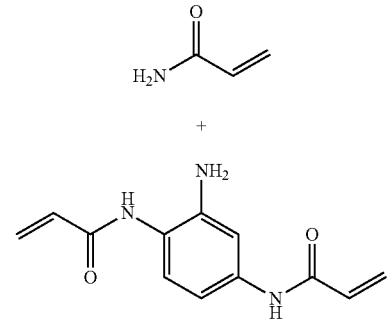

[Chemical Formula 5]

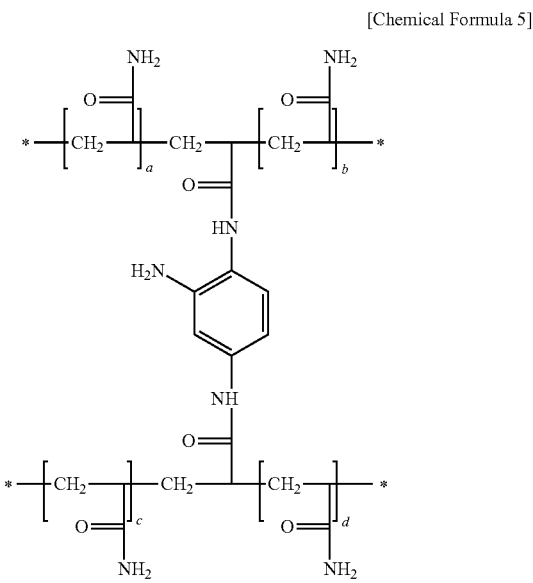

The crosslinking point of the polymeric gel represented by Chemical Formula 5 may form an amide-substituted benzotriazole intermediate residue, as represented by Chemical Formula 6 in c) of FIG. 1, by a reaction with nitrogen monoxide. The intermediate residue may be hydrolyzed to be decomposed into a benzotriazole residue and a carboxylic acid residue, respectively, as represented by Chemical Formula 7 in d) of FIG. 1.

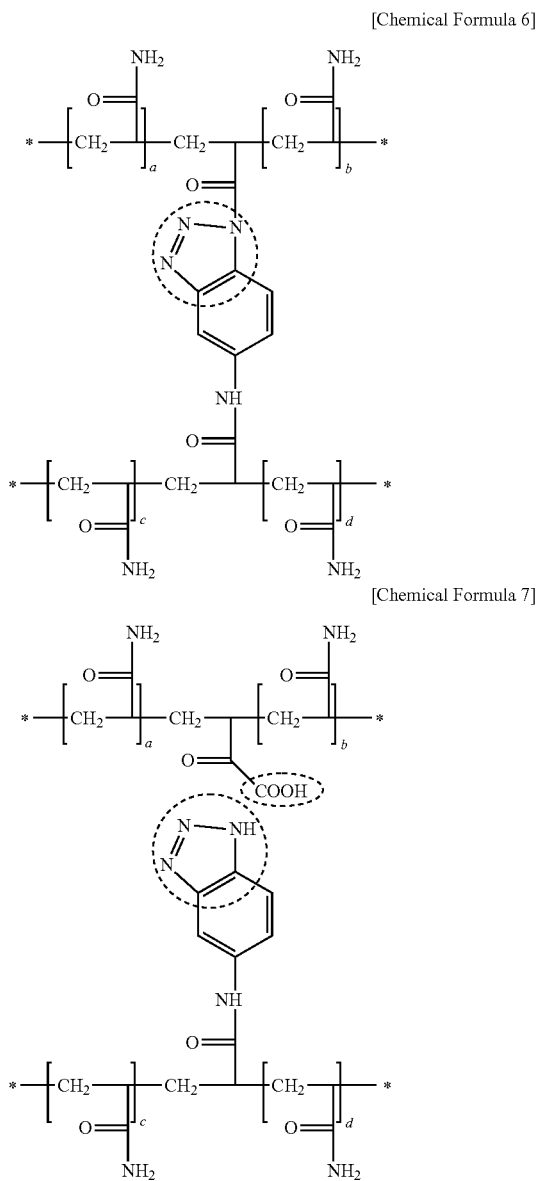

[Chemical Formula 6]

[Chemical Formula 7]

Here, in Chemical Formulae 5 to 7, a, b, c, and d are defined by the moles of the monomer.

Meanwhile, the polymeric gel according to an exemplary embodiment of the present invention may be preferably a hydrogel. The hydrogel is also referred to as a hydrated gel, and represents a three-dimensional reticular structure formed by crosslinking a hydrophilic polymer by a covalent or non-covalent bond. The hydrogel is characterized in that it is not dissolved in an aqueous solution but absorbs a large amount of water to swell, and generally contains a large amount of moisture and has intermediate properties between liquid and solid.

That is, the hydrogel according to an exemplary embodiment of the present invention may include a polymer main chain and a crosslinking point which is crosslinked to the polymer main chain.

In an exemplary embodiment of the present invention, the polymer main chain may be used without a particular limitation as long as it is commonly used in the art, and specifically, for example, the polymer main chain of the hydrogel may be derived from a monofunctional hydrophilic monomer. Here, the monofunctional hydrophilic monomer may be a hydrophilic acrylic monomer, and as a specific example, the hydrophilic acrylic monomer may be one or two or more selected from the group consisting of hydroxyalkyl methacrylate having 1 to 15 carbon atoms in which 1 to 3 hydroxy groups are substituted, hydroxyalkyl acrylate having 1 to 15 carbon atoms in which 1 to 3 hydroxy groups are substituted, acrylamide, vinyl pyrrolidone, glycerol methacrylate, acrylic acid, methacrylic acid, and the like. More specifically, for example, the hydrophilic acrylic monomer may be one or two or more selected from the group consisting of 2-hydroxyethyl methacrylate (HEMA), acrylamide, N,N-dimethyl acrylamide (DMA), N-vinyl pyrrolidone (NVP), glycerol monomethacrylate (GMMA), methacrylic acid (MAA), and the like, but not necessarily limited thereto.

The crosslinking point of the hydrogel may be dissociated by a reaction with nitrogen monoxide, when all crosslinking points are dissociated, the crosslinked structure is completely cleaved, so that the polymeric gel may be converted to a sol form, and the hydrogel having a drug carried inside thereby has an advantage of particularly rapidly releasing the drug.

Meanwhile, the hydrogel according to an exemplary embodiment of the present invention may further include a second crosslinking point derived from a polyfunctional crosslinker containing two or more functional groups. This second crosslinking point may be also crosslinked to the polymer main chain, and the second crosslinking point may have a chemical structure which does not respond to nitrogen monoxide. Though the hydrogel according to this embodiment reacts with a high concentration of nitrogen monoxide, a certain amount or more of crosslinks remain, thereby maintaining the form of the hydrogel even at the time of swelling, and the hydrogel swells by the reaction with nitrogen monoxide to increase a mesh size. In addition, the hydrogel having a drug carried inside thereby may respond to nitrogen monoxide to easily release the drug.

The second crosslinking point as such may be derived from a polyfunctional crosslinker containing two or more functional groups, in which the polyfunctional crosslinker containing two or more functional groups is not particularly limited as long as it is commonly used. Specifically, the polyfunctional crosslinker containing two or more functional groups may be used as long as it contains two or more acryl groups, methacryl groups, or vinyl groups, and as a non-limited example, the polyfunctional crosslinker may be any one or two or more selected from the group consisting of ethylene glycol diacrylate, ethylene glycol dimethacrylate, poly(ethylene glycol) diacrylate, poly(ethylene glycol) dimethacrylate, 1,6-hexanediol diacrylate, 1,6-hexanediol dimethacrylate, tri(propylene glycol) diacrylate, tri(propylene glycol) dimethacrylate, trimethylolpropane triacrylate, trimethylolpropane trimethacrylate, pentaerythritol diacrylate, pentaerythritol dimethacrylate, pentaerythritol triacrylate, pentaerythritol trimethacrylate, pentaerythritol tetraacrylate, pentaerythritol tetramethacrylate, dipentaerythritol diacrylate, dipentaerythritol dimethacrylate, dipentaerythritol triacrylate, dipentaerythritol trimethacrylate, dipentaerythritol tetraacrylate, dipentaerythritol tetramethacrylate, dipentaerythritol pentaacrylate, dipentaerythritol pentamethacrylate, dipentaerythritol hexaacrylate, dipentaerythritol hexamethacrylate, and the like, but is not necessarily limited thereto.

In an exemplary embodiment of the present invention, the size and form of the hydrogel is not greatly limited, and the size may be adjusted to a desired size by adjusting ratios of the monofunctional hydrophilic monomer and the monomer containing a plurality of functional groups including the o-phenylenediamine residue, and the like and the form may also be easily changed according to the purpose.

As a specific example, the hydrogel according to an exemplary embodiment of the present invention may have a diameter from several nm to tens of cm and may be in the form of particles, a capsule, a patch, or the like, but not limited thereto.

Hereinafter, a method of preparing a hydrogel will be described, as a specific example of the above-described polymeric gel.

Specifically, the method of preparing a hydrogel may include: a) polymerizing a mixture of a monofunctional hydrophilic monomer and a monomer containing a plurality of functional groups including an o-phenylenediamine residue; and b) separating the hydrogel formed by the polymerization.

The hydrogel including a crosslinking point which is dissociated in response to nitrogen monoxide may be prepared thereby. The thus-prepared hydrogel has advantages that the polymeric gel may respond to nitrogen monoxide to remove unnecessary nitrogen monoxide inside and outside the body, and also a crosslinking point forming a crosslinked structure with a polymer chain of the hydrogel is dissociated by response to nitrogen monoxide in an environment in which nitrogen monoxide is present, thereby releasing a drug carried inside the hydrogel.

First, a step a) of polymerizing a mixture of a monofunctional hydrophilic monomer and a monomer containing a plurality of functional groups including an o-phenylenediamine residue may be performed.

In an exemplary embodiment of the present invention, the monomer containing a plurality of functional groups including an o-phenylenediamine residue may satisfy the following Chemical Formula 2:

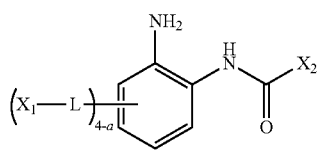

[Chemical Formula 2]

wherein L is —NHCO—, —RO—, —ORO—, or —RO(C=O)— in which R is a direct bond, a linear or branched alkylene group having 1 to 20 carbon atoms, an arylene group having 6 to 30 carbon atoms, a cycloalkylene group having 5 to 30 carbon atoms, an arylene group having 6 to 30 carbon atoms which is substituted with a linear or branched alkyl group having 1 to 20 carbon atoms, or a linear or branched alkylene group having 1 to 20 carbon atoms which is substituted with an aryl group having 6 to 30 carbon atoms, $X_1$ and $X_2$ are independently of each other —CH=CH$_2$ or —C(CH$_3$)=CH$_2$, and a is a real number of 0 to 3.

In a preferred exemplary embodiment, the monomer containing a plurality of functional groups including an o-phenylenediamine residue may satisfy the following Chemical Formula 3. By satisfying this, the crosslinker which is dissociated by hydrolysis in response to nitrogen monoxide may be easily synthesized, and the polymeric gel may be easily prepared. In addition, selectivity and sensitivity to nitrogen monoxide may be excellent.

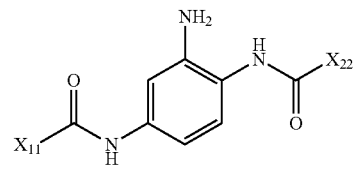

[Chemical Formula 3]

wherein $X_{11}$ and $X_{22}$ are independently of each other —CH=CH$_2$ or —C(CH$_3$)=CH$_2$.

The monofunctional hydrophilic monomer according to an exemplary embodiment of the present invention may be the same as that described above, and the monofunctional hydrophilic monomer may be a hydrophilic acrylic monomer. As a specific example, the hydrophilic acrylic monomer may be one or two or more selected from the group consisting of hydroxyalkyl methacrylate having 1 to 15 carbon atoms in which 1 to 3 hydroxy groups are substituted, hydroxyalkyl acrylate having 1 to 15 carbon atoms in which 1 to 3 hydroxy groups are substituted, acrylamide, vinyl pyrrolidone, glycerol methacrylate, acrylic acid, methacrylic acid, and the like. More specifically, for example, the hydrophilic acrylic monomer may be one or two or more selected from the group consisting of 2-hydroxyethyl methacrylate (HEMA), acrylamide, N,N-dimethyl acrylamide (DMA), N-vinyl pyrrolidone (NVP), glycerol monomethacrylate (GMMA), methacrylic acid (MAA), and the like, but not necessarily limited thereto.

In step a), a mixed ratio of the monofunctional hydrophilic monomer and the monomer containing a plurality of functional groups including an o-phenylenediamine residue may be adjusted differently depending on the size, physical properties, and the like of the hydrogel to be prepared. As a non-limited example, the monofunctional hydrophilic monomer and the monomer containing a plurality of functional groups including an o-phenylenediamine residue may be mixed at a molar ratio of 1000:0.289 to 2.89, and more preferably at a molar ratio of 1000:0.482 to 0.964. Within the range, the hydrogel may be effectively formed, and may effectively swell after response to nitrogen monoxide to rapidly release a drug at the time of releasing the drug.

Meanwhile, in an exemplary embodiment of the present invention, the mixture of step a) may further include a polyfunctional crosslinker. Here, the polyfunctional crosslinker is crosslinked with a polymer main chain to form a crosslinked structure, but may not be responsive to nitrogen monoxide, and since it is not responsive to nitrogen monoxide, the hydrogel may maintain a certain degree or more of mechanical strength and form even in the case of reacting with a high concentration of hydrogel.

The polyfunctional crosslinker as such is not particularly limited as long as it is commonly used. Specifically, the polyfunctional crosslinker containing two or more functional groups may be used as long as it contains two or more acryl groups, methacryl groups, or vinyl groups, and as a non-limited example, the polyfunctional crosslinker may be any one or two or more selected from the group consisting of ethylene glycol diacrylate, ethylene glycol dimethacrylate, poly(ethylene glycol) diacrylate, poly(ethylene glycol) dimethacrylate, 1,6-hexanediol diacrylate, 1,6-hexanediol dimethacrylate, tri(propylene glycol) diacrylate, tri(propylene glycol) dimethacrylate, trimethylolpropane triacrylate, trimethylolpropane trimethacrylate, pentaerythritol diacrylate, pentaerythritol dimethacrylate, pentaerythritol triacrylate, pentaerythritol trimethacrylate, pentaerythritol tetraacrylate, pentaerythritol tetramethacrylate, dipentaerythritol diacrylate, dipentaerythritol dimethacrylate, dipentaerythritol triacrylate, dipentaerythritol trimethacrylate, dipentaerythritol tetraacrylate, dipentaerythritol tetramethacrylate, dipentaerythritol pentaacrylate, dipentaerythritol pentamethacrylate, dipentaerythritol hexaacrylate, dipentaerythritol hexamethacrylate, and the like, but is not necessarily limited thereto.

An amount of the polyfunctional crosslinker added may be adjusted differently depending on the physical properties of the hydrogel to be desired, and as an example, the polyfunctional crosslinker may be added at 0.0001 to 0.1 mole times, and more preferably 0.005 to 0.03 mole times, relative to 1 mole of the monofunctional hydrophilic monomer. Within the range, mechanical strength is imparted to the hydrogel, while response sensitivity to nitrogen monoxide may not be lowered. In addition, at the time of drug delivery, release of the drug carried inside the hydrogel may not be prevented.

In addition, of course, the mixture of step a) may also further include an initiator and a catalyst for a crosslinking reaction, and it is known to those skilled in the art that any initiator and catalyst may be used without limitation as long as they are commonly used in the art.

Meanwhile, in an exemplary embodiment of the present invention, the mixture of step a) may be performed in a water phase. That is, a mixture of the monofunctional hydrophilic monomer and the monomer containing a plurality of functional groups including an o-phenylenediamine residue is dissolved in water, and then the polymerization reaction may be performed, thereby preparing the hydrogel containing water inside.

Thereafter, when the polymerization reaction is completed, a step b) of separating the hydrogel formed by the polymerization may be performed. A separation method is not particularly limited as long as the hydrogel may be separated without being damaged.

Meanwhile, the present invention may provide a drug delivery system including the polymeric gel, in which a drug is carried in the above-described polymeric gel and then the drug carried inside the polymeric gel may be released by a reaction with nitrogen monoxide. As described later, the polymeric gel carrying the drug may be prepared by mixing a drug at the time of forming the gel to form the polymeric gel, and the polymeric gel carrying the drug reacts with nitrogen monoxide so that the crosslinking point is dissociated, whereby the crosslinked structure may be decomposed to release the drug carried inside the polymeric gel.

In addition, the present invention provides a method of adjusting a mesh size of a reticular structure by including an o-phenylenediamine residue as the crosslinking point of the reticular structure. As described above, in the polymeric gel according to an exemplary embodiment of the present invention, the crosslinking point may be dissociated by a reaction with nitrogen monoxide, thereby cleaving the crosslinked structure to increase the mesh size of the reticular structure. The mesh size as such may be adjusted depending on a ratio of the crosslinking point of the reticular structure, or may be selectively adjusted by cleaving the crosslinked structure by nitrogen monoxide. That is, some crosslinking points are dissociated by nitrogen monoxide, thereby selectively adjusting the mesh size, which is adjustable by a concentration of nitrogen monoxide and the like.

Also, the present invention provides a method of detecting nitrogen oxides in exhaust gas, using the polymeric gel described above. In the polymeric gel according to the present invention, the crosslinked structure collapses by a reaction with nitrogen oxides, in particular nitrogen monoxide, so that the mechanical physical properties thereof may be deteriorated, and the presence of nitrogen monoxide and the concentration thereof may be detected by change in the form, modulus of elasticity, loss factor, and the like of the hydrogel.

As a specific example, the nitrogen oxides in the exhaust gas may be detected by a swelling ratio, and the polymeric gel may include 450 wt % or more of moisture based on a dried weight of the polymeric gel. It is preferred to include 1,000 wt %, more preferably 1,400 wt % of moisture, for effectively swelling the polymeric gel. Here, the upper limit of moisture is not particularly limited, but may be 4,650 wt % or less. Here, the amount of moisture may be calculated from the following equation: amount of moisture=[(weight of polymeric gel after moisture absorption−dried weight of polymeric gel)/dried weight of polymeric gel]×100.

In addition, the present invention provides a contact lens including the above-described polymeric gel. The contact lens may be for inhibiting angiogenesis, and patients having a disease of angiogenesis emits nitrogen monoxide from their eyeball so that the disease is worsen. Accordingly, when the contact lens including the polymeric gel according to the present invention is used, nitrogen monoxide is captured in the polymeric gel to inhibit the angiogenesis disease.

Hereinafter, the polymeric gel, a method of preparing the same, and an article including the same according to the present invention will be described in detail, by the Examples. However, the following Examples are only a reference for describing the present invention in detail, and the present invention is not limited thereto, and may be implemented in various forms. In addition, unless otherwise defined, all technical terms and scientific terms have the same meanings as those commonly understood by those skilled in the art to which the present invention pertains. The terms used herein is only for effectively describing a certain exemplary embodiment, and not intended to limit the present invention. In addition, the singular form used in the specification and claims appended thereto may be intended to also include a plural form, unless otherwise indicated in the context. Further, unless otherwise stated, the unit of added materials herein may be wt %.

[Preparation Example 1] Synthesis of Crosslinker (NOCCL)

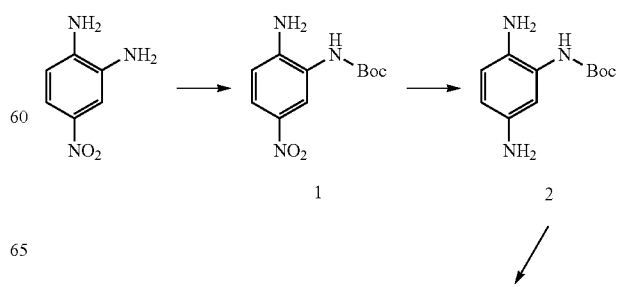

-continued

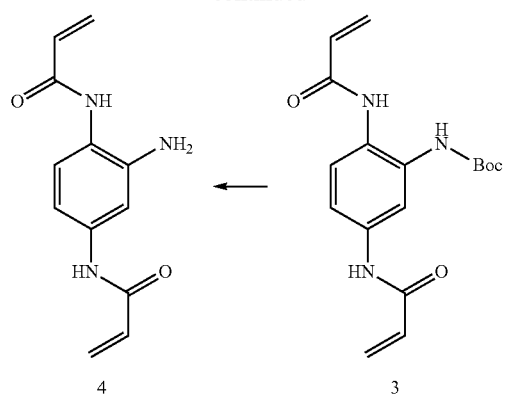

[Example 1] Synthesis of Nitrogen Monoxide-Responsive Hydrogel (NOR Gel)

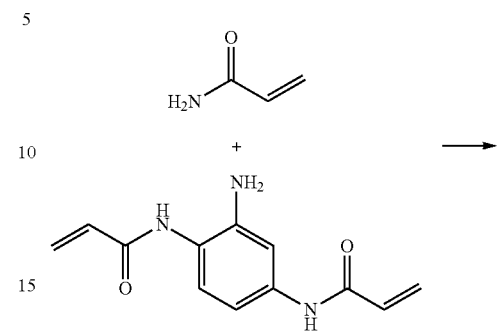

Compound 1: At 25° C., di-t-butyldicarbonate (2.85 mg, 13.06 mmol) was added dropwise to a reaction solution in which 4-nitro-o-phenylenediamine (1 g, 6.53 mmol) and guanidine hydrochloride (15 mol %) were dissolved in 20 ml of ethanol, and the solution was vigorously stirred for 40 hours while maintaining the temperature at 35 to 40° C. After completion of the reaction, an organic solvent in the reaction solution was evaporated under reduced pressure, extraction was performed three times with ethyl acetate, and the resultant was dried and purified by silica gel column chromatography, thereby obtaining Compound 1 (yield: 74 wt %, 1.22 g). In the above scheme, Boc is —COO—t-$C_4H_9$.

Compound 2: Under a nitrogen atmosphere, 10 wt % of a palladium-loaded carbon catalyst (10 wt % Pd/C, 60 mg) was added to a solution (in anhydrous tetrahydrofuran (dry THF), 10 ml) of Compound 1 (0.6 g), the atmosphere was converted from nitrogen to hydrogen (40 psi), and the solution was stirred at 25° C. for 36 hours. After completion of the reaction, Pd/C was removed by filtering using celite 545 AW, and the filtrate was dried, thereby obtaining Compound 2 without further purification (yield: 96 wt %, 423 mg).

Compound 3: At 25° C., acryloyl chloride (648.05 mg, 7.16 mmol) was added dropwise to a reaction solution in which Compound 2 (400 mg, 1.79 mmol) and triethylamine (723.16 mg, 7.16 mmol) are dissolved in anhydrous THF, and then was vigorously stirred at 25° C. for 24 hours. After completion of the reaction, an organic solvent in the reaction solution was evaporated under reduced pressure, extraction was performed three times with ethyl acetate, and the resultant was dried and purified by alumina chromatography, thereby obtaining Compound 3 (yield: 64 wt %, 379 mg).

Compound 4 (NOCCL): In an ace bath, 3 ml of 4M HCl dioxane solution was added to a solution (in 3 ml of anhydrous THF) of Compound 3 (200 mg, 0.60 mmol), and then was vigorously stirred at 25° C. for 24 hours. After completion of the reaction, an organic solvent in the reaction solution was evaporated under reduced pressure, extraction was performed three times with ethyl acetate, and the resultant was dried and purified by alumina chromatography, thereby obtaining Compound 4 (yield: 21 wt %, 29.11 mg).

Compound 4 (NOCCL, 10 mg, 43.3 mmol) was dissolved in 100 μl of an 10 vol % aqueous ethanol solution, water was added to the solution to dilute the solution so that the concentration of Compound 4 is 0.0625 w/v %, and 10 μl of this aqueous ethanol solution of Compound 4 having a concentration of 0.0625 w/v % was mixed with 10 μl of 40 w/v % aqueous acrylamide solution in a 1.25 ml micro test tube (e-tube). Thereafter, 1 μl of 8 w/v % aqueous ammonium persulfate (APS) solution and 1 μl of 4 w/v % aqueous tetramethylethylenediamine (TEMED) solution were added to the e-tube and subjected to vortex treatment for uniform gelation to synthesize an NOR gel. Here, w/v % means % by weight/volume.

[Example 2] Synthesis of NOR Gel Nanoparticles

Nano-sized NOR gel nanoparticles were prepared in the same manner as in Example 1, except that 10 μl of an aqueous ethanol solution of Compound 4 (NOCCL) having a concentration of 0.016 w/v % and 10 μl of aqueous acrylamide solution having a concentration of 20 w/v % were used. The size distribution and the scanning electron microscope image thereof are shown in FIG. 9.

[Comparative Example 1] Synthesis of Control Hydrogel (CTL Gel)

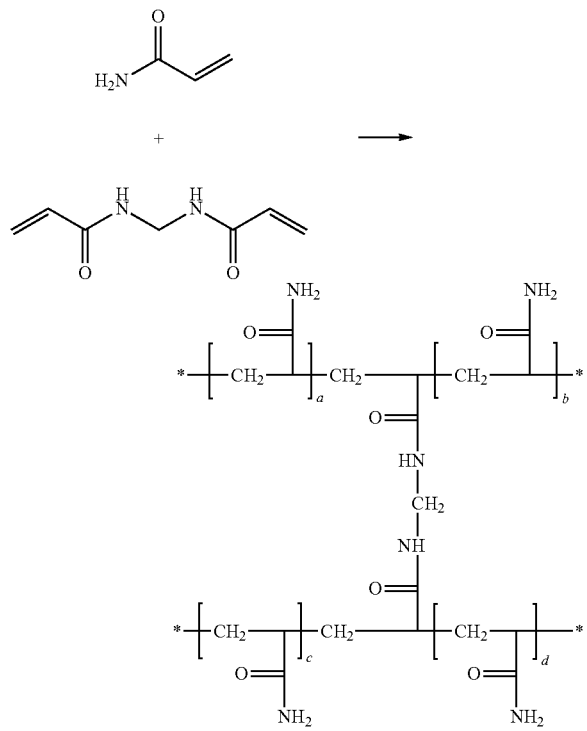

All processes proceeded in the same manner as in Example 1, except for using N,N'-methylene bisacrylamide (40.38 mmol) instead of Compound 4 (NOCCL).

[Physical Property Evaluation]

1) Experiment for Response to Gaseous Nitrogen Monoxide

In addition, reactivity of nitrogen monoxide was evaluated by directly exposing the product of Example 1 (NOR gel) and the product of Comparative Example 1 (CTL gel) to nitrogen monoxide or an argon gas.

In order to install the device, a commercially available plastic box (a width of 10 cm×a length of 13 cm×a height of 5 cm) was punched with a hole having a diameter of 0.4 cm to allow gas to get in and out, as shown in FIG. 2. Thereafter, the gels of Example 1 and Comparative Example 1 were fixed on a wall inside the box using a corkboard, nitrogen monoxide or an argon gas were injected thereto for 10 minutes, and the form of the hydrogel was monitored. If necessary, an elongation of the hydrogel by gravity was measured, using a fishhook (a length of 2.7 mm).

As a result, after injecting nitrogen monoxide, the gel of Example 1 reacted to nitrogen monoxide and began to droop down within 4 minutes, and a stretch degree was gradually increased according to a nitrogen monoxide injection time, as shown in FIG. 2. From this result, it was found that NOCCL in the hydrogel is dissociated by the reaction with a nitrogen monoxide gas, and the mechanical properties of the hydrogel was deteriorated. However, the shape of the hydrogel of Comparative Example 1 was not changed, but the color of the hydrogel was changed to light yellow, which is because the nitrogen monoxide gas reacted with oxygen in the hydrogel to be converted to $NO_2$, and this $NO_2$ was captured inside the hydrogel of Comparative Example 1.

Meanwhile, when the argon gas was injected, the shapes of the hydrogels of both Example 1 and Comparative Example 1 were not changed.

By the gas injection experiment as such, it was found that the NOR gel of Example 1 had rapid reactivity, high sensitivity, and high selectivity to gaseous nitrogen monoxide also.

2) Experiment for Response to Nitrogen Monoxide Dissolved in Water

First, a nitrogen monoxide solution was prepared according to the previously reported method. Specifically, 10 ml of distilled water was added to a 40 ml vial, bubbled with a nitrogen gas for 30 minutes, and transferred to a nitrogen monoxide device. The nitrogen monoxide solution was washed with an argon gas to remove oxygen, and the nitrogen gas was circulated for 30 minutes under a pressure of 1.36 atm. The saturated nitrogen monoxide solution was confirmed to have a concentration of 1.88 mM at 20° C., and all nitrogen monoxide solutions were freshly prepared immediately before the experiment.

Next, an initial weight of the hydrogels of Example 1 and Comparative Example 1 was measured, and for a gel swelling test, the hydrogel was incubated in 50 μl of water in a 1.25 ml e-tube. Thereafter, this hydrogel was incubated in 500 μl of water or a nitrogen monoxide solution (1.57, 15.7, 157, and 1570 μM) for 2, 4, 12, 24, and 48 hours, and then the weight was measured.

A swelling ratio (S) may be defined as a weight of a hydrogel increased by moisture absorption, and was calculated by the following equation:

$$S \text{ (wt \%)} = (M_f - M_i)/M_i$$

Relative swelling ratio $(\%) = S/S_0$ wherein $M_i$ is an initial weight of a dried hydrogel, $M_f$ is a weight of the hydrogel after a swelling experiment in a nitrogen monoxide solution, S is a swelling ratio in the nitrogen monoxide solution, and $S_0$ is a swelling ratio in water calculated in the same manner as in the above equation after a swelling experiment in water at 0° C.

As a result, when the gel of Example 1 was not exposed to nitrogen monoxide, that is, was incubated in water, the gel of Example 1 gradually swelled up to 24 hours and then did not swell any more. This is a general behavior of a hydrogel and the hydrogel absorbs water and swells to be in a saturated state. Meanwhile, the gel of Example 1 incubated in the nitrogen monoxide solution gradually swelled and the polymer network was dissociated by cleavage of NOCCL which is the crosslinking point. Thus, a large amount of water was absorbed in the hydrogel network and continuously swelled until the hydrogel was saturated. The swelling ratio of the gel of Example 1 at a highest nitrogen monoxide concentration (1570 μM) was 1.5 times higher than the swelling ratio of the gel which was not exposed to nitrogen monoxide, and the swelling degree greatly depends on the nitrogen monoxide concentration, as shown in a of FIG. 3.

However, as shown in b of FIG. 3, the gel of Comparative Example 1 using a non-cleavable crosslinker had a swelling ratio which does not differ greatly from the swelling ratio of the gel which was not exposed to nitrogen monoxide regardless of the nitrogen monoxide concentration.

3) Measurement of Hydrogel Form

A scanning electron microscope (SEM, JSM 7410 F, JEOL) was used to observe the form of the Example 1 before and after the reaction with a nitrogen monoxide solution (1570 μM). After reaction with the nitrogen monoxide solution at 25° C. for 24 hours, the gel was lyophilized at −80° C. overnight, the cross section thereof was cut and coated with platinum (Pt), and an SEM image was measured.

As a result, as shown in c of FIG. 4, the gel of Example 1 showed a smooth surface having a polymer network structure which was crosslinked before the reaction with nitrogen monoxide. However, after the reaction with nitrogen monoxide, the gel of Example 1 had fine pores inside (d of FIG. 4), and this is determined to be because nitrogen monoxide dissociates the crosslinking point. Accordingly, it is expected that water rapidly enters to a gel through this pore, and a drug payload inside the gel may be rapidly released.

4) Evaluation of Rheological Properties

In order to quantitatively analyze the influence of nitrogen monoxide, a rheological parameter, a modulus of elasticity (G'), and a loss factor (G") were analyzed to examine the viscoelasticity of the hydrogel. The test was performed under the conditions of a fixed temperature, a strain, and a variable frequency.

Specifically, the rheological properties of Example 1 and Comparative Example 1 were evaluated using a rheometer (Malvern Kinexus+, England). The gel was incubated in a nitrogen monoxide solution or water, and the rheological properties of the gel when being subjected to 0.5% complex shearing deformation in a frequency range of 0.1 to 10 Hz, were analyzed. In addition, G' and G" were measured, and the rheological properties as a function of the applied frequency were evaluated.

Generally, when G' is irrelevant to stimulation, the hydrogel is regarded as a material having no reaction, and when G' depends on stimulation, the hydrogel is regarded as being stimulation-reactive. In addition, when G' is larger than G", the hydrogel is regarded as being highly structured into a gel-type structure, and when G' is similar to G", the network structure of the hydrogel collapses and has the same structure as a fluid.

In Example 1, as shown in FIG. 5, it was found that as the nitrogen monoxide concentration was increased, the value of G' was gradually decreased, so that the mechanical strength of the NOR gel was decreased, and the structure collapsed. In addition, as shown in FIG. 6, in Example 1, it was found that before the reaction with nitrogen monoxide, G' was much larger than G", but as the nitrogen monoxide concentration was increased, the values of G' and G" became similar to each other. However, as shown in FIG. 5, it was found that in Comparative Example 1, the value of G' was relatively high and even in the case of incubation in a highly concentrated nitrogen monoxide solution, the G' value was hardly changed, and thus, the hydrogel structure was maintained to be stable.

5) Experiment for Drug Release

In order to examine whether the NOR gel may be applied as a nitrogen monoxide-reactive drug delivery flatform, a bovine serum albumin (BSA) labelled with fluorescein isothiocyanate (FITC) was used as a model protein for a release experiment. Specifically, BSA (100 µl, 2 mg/ml in 4 w/v % aqueous NaHCO$_3$ solution) was mixed with FITC (10 µl, 1 mg/ml in H$_2$O) and stirred overnight. This solution was dialyzed to water with a dialyzing diaphragm (MWCO 3.5 k) to remove unreacted FITC, and lyophilized at −80° C. to prepare BSAS labelled with FITC (BSA-FITC).

10 µl of a 40 w/v % aqueous acrylamide solution, 10 µl of a 0.0625 wt % aqueous ethanol solution of Compound 4, and 5 µl of an aqueous BSA-FITC (10 mg/ml) solution were mixed in a 1.25 ml e-tube, and 1 µl of a 5 w/v % aqueous APS solution and 1 µl of a 10 w/v % aqueous TEMED solution were added to this mixed solution. Subsequently, the mixed solution was subjected to vortex treatment for uniform gelation to prepare a hydrogel containing BSA-FITC. The hydrogel containing BSA-FITC was washed with 1 ml of water three times, and the release profile was evaluated with a time function (ex/em 485/510 nm). A hydraulic size of the hydrogel was measured with Zetasizer (Nano S90, Malvern, United Kingdom), and the size and shape of the hydrogel were measured with a transmission electron microscope (TEM, JEM-1011, JEOL, Tokyo, Japan). Also, the sample was stained with a 0.5 w/v % aqueous uranyl acetate solution, and loaded on a 400 mesh copper (Cu) grid before analysis.

In addition, a control hydrogel was prepared in the same manner as the above, except that N,N'-methylenebisacrylamide was used as a crosslinker instead of Compound 4, as a control of the hydrogel containing BSA-FITC.

Each of the hydrogels prepared above was slowly stirred in water or a nitrogen monoxide solution (18.6 µM), while a BSA release degree according to a stirring time was observed.

As a result, as shown in FIG. 7, the hydrogel containing BSA-FITC released BSA more rapidly when treated with the nitrogen monoxide solution than when treated with water. However, the BSA release rates of the control hydrogen when treated with the nitrogen monoxide solution and when treated with water were almost similar.

6) Swelling of Hydrogel in Nitrogen Monoxide Production Cultured Cell

A swelling behavior of the hydrogel depending on the reaction with nitrogen monoxide secreted from cells cultured in vitro was analyzed. For this, RAW 264.7 cells and NIH/3T3 cells were used, and the RAW 264.7 cells are one type of a rat macrophage which produces nitrogen monoxide when stimulated by lipopolysaccharides (LPS) and produces about 14 µM of nitrogen monoxide without LPS treatment, but produces about 38 µM of nitrogen monoxide when treated with LPS. In addition, the NIH/3T3 cells are fibroblasts, and are cells which do not produce nitrogen monoxide even when stimulated by LPS.

Specifically, the RAW 264.7 cells and the NIH/3T3 cells were cultured in a Dulbecco's Modified Eagle's Medium (DMEM) containing a 10% fetal bovine serum (FBS), respectively. The cells were inoculated at a density of 400,000 cells/well in a 6-well plate, and were cultured for 24 hours. After exchanging the medium, 10 µl of LPS (0.01 mg/ml) was added to each well, and cultured for 30 minutes. The hydrogel was added to the well carefully, and cultured for 24 hours. The weight of the hydrogel was measured and a relative swelling ratio was calculated. The nitrogen monoxide concentration secreted from the cells was measured with griess analysis.

As a result, as shown in FIG. 8, when the gel of Example 1 was cultured with the cells which were not treated with LPS, the gel of Example 1 hardly swelled, and when cultured with the RAW 264.7 cells treated with LPS, the hydrogel greatly swelled. However, the gel of Comparative Example 1 swelled to a similar degree regardless of LPS treatment. When the same experiment was performed using the NIH/3T3 cells, both of the gels of Example 1 and Comparative Example 1 had a similar degree of swelling.

Hereinafter, the preferred exemplary embodiment of the present invention has been described, however, various modifications, alteration, and equivalents may be used in the present invention, and it is apparent that the above exemplary embodiments may be properly modified and identically applied. Therefore the above description does not limit the scope of the present invention which is defined by the claims which follow.

The invention claimed is:

1. A polymeric gel comprising a crosslinking point which is dissociated in response to nitrogen monoxide.

2. The polymeric gel of claim 1, wherein the crosslinking point is derived from o-phenylenediamine.

3. The polymeric gel of claim 2, wherein the crosslinking point satisfies the following Chemical Formula 1:

[Chemical Formula 1]

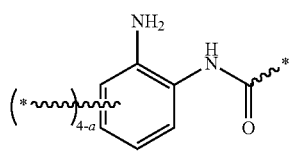

wherein * is a bonding site, and a is a real number of 0 to 3.

4. The polymeric gel of claim 1, wherein the polymeric gel is a hydrogel.

5. The polymeric gel of claim 4, wherein a polymer main chain of the hydrogel is derived from a monofunctional hydrophilic monomer.

6. The polymeric gel of claim 5, wherein the hydrogel further includes a second crosslinking point derived from a polyfunctional crosslinker containing two or more functional groups.

7. The polymeric gel of claim 4, wherein the hydrogel is in a form of particles, a capsule, or a patch.

8. A drug delivery system comprising the polymeric gel of claim 1.

9. A method of detecting nitrogen oxides in an exhaust gas, by using the polymeric gel of claim 1.

10. The method of detecting nitrogen oxides in an exhaust gas of claim 9, wherein the nitrogen oxides are nitrogen monoxide.

11. The method of detecting nitrogen oxides in an exhaust gas of claim 9, wherein the polymeric gel includes 450 wt. % or more of moisture relative to a dried weight of the polymeric gel.

12. A contact lens comprising the polymeric gel of claim 1.

13. The contact lens of claim 12, wherein the contact lens is for inhibiting angiogenesis.

* * * * *